(12) United States Patent
Hamamoto et al.

(10) Patent No.: US 6,730,046 B1
(45) Date of Patent: May 4, 2004

(54) BODY FLUID SAMPLING APPARATUS

(75) Inventors: Katsumi Hamamoto, Kyoto (JP);
Atsushi Murakami, Kyoto (JP);
Hiroshi Hyodo, Kyoto (JP)

(73) Assignee: Arkray, Inc., Kyoto (JP)

( * ) Notice: Subject to any disclaimer, the term of this patent is extended or adjusted under 35 U.S.C. 154(b) by 226 days.

(21) Appl. No.: 10/089,296

(22) PCT Filed: Sep. 28, 2000

(86) PCT No.: PCT/JP00/06745

§ 371 (c)(1),
(2), (4) Date: Mar. 27, 2002

(87) PCT Pub. No.: WO01/22882

PCT Pub. Date: Apr. 5, 2001

(30) Foreign Application Priority Data

Sep. 29, 1999  (JP) .......................................... 11/276451

(51) Int. Cl.$^7$ ................................................ A61B 5/15
(52) U.S. Cl. ...................................... 600/583; 606/182
(58) Field of Search ................................ 600/573–584; 606/181–189

(56) References Cited

U.S. PATENT DOCUMENTS 5,350,392 A  *  9/1994  Purcell et al. .............. 606/182
5,368,047 A     11/1994 Suzuki et al.
5,666,966 A  *  9/1997  Horie et al. ................. 600/583
5,916,230 A     6/1999  Brenneman et al.
6,086,545 A  *  7/2000  Roe et al. .................... 600/583

FOREIGN PATENT DOCUMENTS

| JP | 05-095937 | 4/1993 |
| JP | 10-127610 | 5/1998 |
| WO | 99/26539 | 6/1999 |

* cited by examiner

Primary Examiner—Max F. Hindenburg
Assistant Examiner—David J. McCrosky
(74) Attorney, Agent, or Firm—Merchant & Gould P.C.

(57) ABSTRACT

A body fluid sampling apparatus (A), comprising a piston (11) provided in a tubular main case (10), a first plunger rod (12) extending into the piston (11) integrally with each other; a first spring (13) elastically energzing the piston (11) toward the upper end side, a second plunger rod (15) installed in the first plunger rod (12) through a second spring (14), a lancet mounted body (16) provided on the second plunger rod (15) and having a lancet (B) mounted therein, a third spring (17) elastically energizing the lancet mounted body (16) toward the upper end side, latch mechanisms (20, 30) suppressing the second plunger rod (15) and first plunger rod (12) when the first plunger rod (12) is moved to the lower end side by he push-down of the piston (11), and a release mechanism (40) for releasing the locked state of the first plunger rod (12) and the second plunger rod (15).

6 Claims, 8 Drawing Sheets

BODY FLUID SAMPLING APPARATUS

TECHNICAL FIELD

The present invention relates to a body fluid sampler for sampling blood for example for measuring the glucose concentration in the blood (hereinafter referred to as "blood sugar level") for example.

BACKGROUND ART

For the treatment of diabetes, it is necessary to maintain the blood sugar level to a normal range. Particularly for the treatment of insulin-dependent diabetes mellitus, a patient needs to conduct insulin injection by himself or herself to keep the blood sugar level to a normal range. In this case, the patient needs to appropriately check the blood sugar level to determine whether the blood sugar level is within the normal range.

Generally, for sampling blood to measure the blood sugar level, use may be made of a portable blood sampler which internally holds, at the tip end of the apparatus, a piercing needle called lancet. In using such a blood sampler, the skin of the patient is instantaneously stabbed by the pointed tip of the lancet. The patient causes the blood sampler to draw blood from the stabbed portion and applies the sampled blood to a blood test piece. In this way, the determination of the blood sugar level can be performed relatively easily.

Such a prior art blood sampler is disclosed in JP-A-5-95937 or JP-A-10-127610 for example. In the prior art sampler disclosed in the former publication, while the tip end of an apparatus body is pressed against the skin of a forearm, a push member is pushed down by a thumb against the repulsive force of a coil spring, thereby stabbing the pointed tip of a lancet into the skin under magnetic action. Thereafter, by retreating the pressing member together with the lancet, the pointed tip of the lancet is removed from the skin. At this time, the air in the interior of the apparatus body undergoes a pressure reduction to cause the stabbed portion to bulge for prompting blood bleeding from the portion stabbed by the lancet.

The prior art sampler disclosed in the latter publication solely utilizes the repulsive force of a spring for pushing down a push member provided at the upper end of an apparatus body to stab the skin with a lancet followed by skin bulging. In use, specifically, the push member provided at the upper end is first pulled up to make the apparatus ready for use. Then, with the tip end of the apparatus pressed against the skin of a forearm for example, the push member is pushed down by a thumb. As a result, the air within the apparatus body escapes to the outside through a non-return valve. When the push member is further depressed, the pointed tip of the lancet stabs the skin. By subsequently removing the thumb from the push member, the force of the spring causes the push member to move back upward. At this time, the interior of the apparatus body undergoes a pressure drop, causing the stabbed portion to bulge. Finally, the push member is pushed down again to relieve the vacuum state within the apparatus body back to the atmospheric pressure, consequently allowing the tip end of the apparatus body to be removed from the skin.

However, the above-described blood samplers have the following drawbacks.

In the prior art sampler disclosed in the former publication, the push member is depressed by one thumb with the tip end of the apparatus body pressed against the skin. In this prior art sampler, however, the air trapped in the apparatus body is compressed, so that a considerable power is required to push down the push member. Moreover, the push member need be pushed down by a considerable stroke. Therefore, the handling of the apparatus by one hand is extremely difficult for a patient having an insufficient force. Further, in depressing the push member with the tip end of the apparatus body pressed against the skin, the patient may fear that the pointed tip of the lancet stabs deeply in the skin particularly when the stroke of the push member is long. Moreover, since the prior art sampler is not provided with means for relieving the vacuum in the apparatus body, blood may splash in removing the pointed tip of the apparatus body from the skin.

Since the prior art sampler disclosed in the latter publication also samples blood only by the operation of the push member, it has the same drawbacks as those of the foregoing prior art sampler. Particularly in this prior art apparatus, the push member need be depressed again to relieve the vacuum state within the apparatus. Therefore, there is a possibility that the lancet stabs the skin again when the push member is excessively depressed.

SUMMARY OF THE INVENTION

It is therefore an object of the present invention to provide a body fluid sampler which is capable of eliminating or at least lessening the above-described problems.

According to the present invention, there is provided a body fluid sampler comprising a cylindrical main case having a first end provided with a first opening and a second end provided with a second opening, a piston inserted in the main case to project from the first opening for movement within the main case airtightly with respect to an inner wall of the main case, a first plunger rod extending integrally from the piston toward said second end, a first elastic member for elastically urging the piston toward said first end, a second plunger rod extending from the first plunger rod toward said second end for movement within the main case with a compressible second elastic member interposed between the first plunger rod and the second plunger rod, a lancet mount associated with the second plunger rod adjacent to said second end for movement within the main case, the lancet mount being provided with a lancet oriented toward said second end, third elastic member for elastically urging the lancet mount toward said first end, latch mechanism which works, when the piston is pushed down for movement toward said second end together with the first plunger rod, for restricting movement of the second plunger rod toward said second end against a pushing force of the second elastic member and for restricting rebounding of the piston and first plunger rod which have been moved toward said second end while allowing the second elastic member to be compressed, and a release mechanism for releasing the first plunger rod and second plunger rod which have been latched by the latch mechanism.

Specifically, the latch mechanism includes a first and a second engagement members each of which has a stopper for stopping a corresponding one of the first and the second plunger rods, a latching elastic member for elastically biasing each of the engagement members toward the corresponding one of the first and the second plunger rods, and engagement portions respectively formed on the first and the second plunger rods, the engagement portions being spaced from each other by a distance which is larger than a distance between the stoppers when the plunger rods are held in an initial state, the release mechanism including a release button for simultaneously releasing the stoppers from the corresponding engagement portions against an elastic biasing force of the latching elastic member.

In the above-described body fluid sampler, the piston moves toward the second end of the main case when it is depressed by the user. As a result, the second elastic member is elastically compressed between the first and the second plunger rods, thereby storing an elastic restoring force. The engagement portion of the first plunger rod engages the stopper of the first engagement member with the first plunger rod biased toward the first end by the second elastic member. The engagement portion of the second plunger rod engages the stopper of the second engagement member with the second plunger rod biased toward the second end by the second elastic member. In this way, the both plunger rods are restricted.

Subsequently, the user pushes the release button of the release mechanism with the second opening of the main case pressed against the skin. When the release button is pushed, the second plunger rod hits or pushes the lancet mount downward due to the elastic force of the second elastic member. Thus, the pointed tip of the lancet instantaneously stabs the skin facing the second opening of the main case. The first plunger rod and the piston return to respective positions before the operation due to the elastic restoring force of the second elastic member and the first elastic member. As a result, the interior of the main case undergoes a pressure reduction to cause the stabbed portion to bulge for prompting blood bleeding from the stabbed portion.

In this way, according to the above-described body fluid sampling apparatus, the preparation for launching the lancet B can be completed by depressing the piston before bringing the second end of the main case into pressing contact with the skin. Since the interior of the main case is held at the atmospheric pressure at this time, even a patient having an insufficient force can conduct the operation by one hand. Moreover, the stroke for depressing the piston is not so long, the user can handle the body fluid sampler easily without anxiety.

According to a preferred embodiment of the present invention, the release button is provided with a push portion projecting from a predetermined portion of a side surface of the main case while keeping airtightness relative to the main case.

With this structure, even when the release button is operated, the airtightness of the main case is maintained. Therefore, just by once pushing the release button, the stabbing of the skin by the lancet and the pressure reduction in the main case can be carried out instantaneously and easily without causing pain to the patient.

According to a preferred embodiment of the present invention, the main case may be provided with a vacuum relief mechanism for relieving a vacuum state within the main case generated by pulling back the piston toward said first end.

Preferably, the vacuum relief mechanism may be provided with a vacuum relief button partially projecting from a predetermined portion of a side surface of the main case, the vacuum relief button being elastically urged in the projecting direction while keeping airtightness of the main case, the vacuum relief button being pushed against the elastic urging force for allowing air passage between inside and outside of the main case.

With this structure, after the stabbing of the skin by the lancet and the pressure reduction in the main case are completed, the pressure in the main case can be returned to the initial atmospheric pressure just by once operating the vacuum relief button. Thus, the second end of the main case formed with the second opening can be easily removed from the skin.

According to a preferred embodiment of the present invention, the piston has an outer circumferential wall provided with an O-ring for closely contacting the inner wall of the main case.

With this structure, the airtightness between the piston and the main case is sufficiently maintained by the O-ring. Therefore, the pressure within the main case can be sufficiently reduced by pulling up the piston to the initial position.

Other features and advantages of the present invention will become clearer from the detailed description given below with reference to the accompanying drawings.

MODE FOR CARRYING OUT THE INVENTION

Preferred embodiments of the present invention will be described below with reference to the accompanying drawings. Throughout the drawings, the elements which are identical or similar to each other are designated by the same reference signs. In the drawings, hollow arrows indicate the direction of the operation by the user, whereas thin arrows indicate the direction of movement of a part or the direction of air flow.

Figure 1:
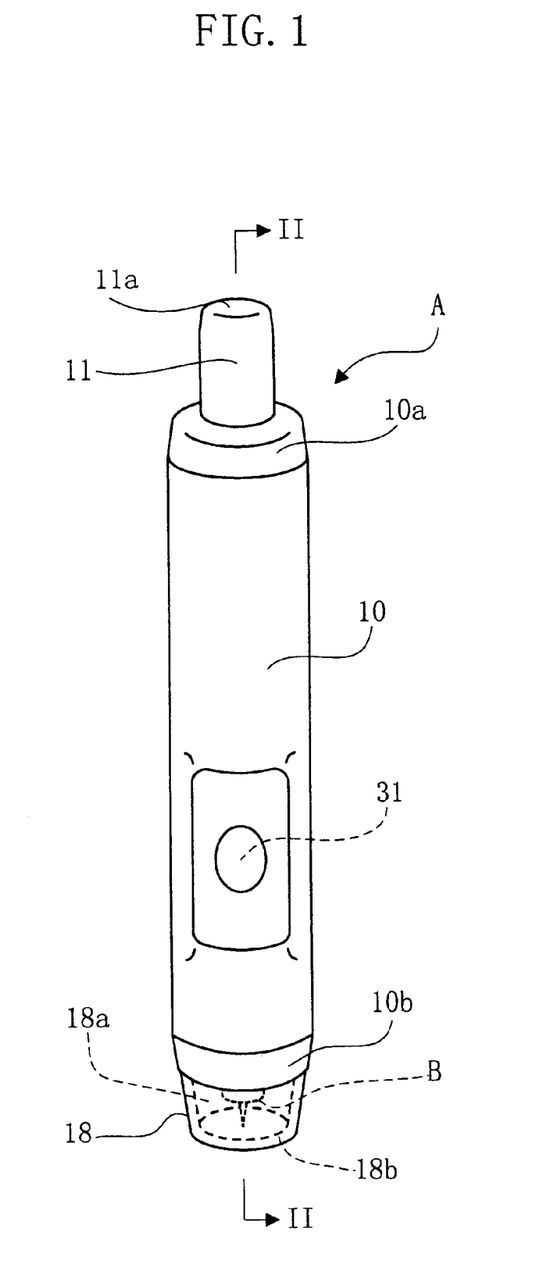
FIG. 1 is a perspective view showing a body fluid sampler embodying the present invention.

First, reference will be made to FIGS. 1 through 3. These figures illustrate a body fluid sampler A, according to the present invention. The body fluid sampler A, which is a portable medical instrument used for the self-sampling of blood for example, holds a lancet B for allowing its instantaneous upward and downward movement. The body fluid sampler A comprises a main case 10, a piston 11, a first and a second plunger rods 12, 15, a first through a third springs 13, 14, 17, a lancet mount 16, a cap 18, a first and a second latch mechanisms 20, 26, a release mechanism 30 and a vacuum relief mechanism 40 and soon. The lancet B comprises a columnar solid body B2 integrally formed with a pointed tip B1 in the form of a needle tip.

The main case 10, which comprises a hollow cylinder of a portable size, has an upper end to which a head cover 10a is attached. The head cover 10a is formed with an upper end opening 10A for inserting the piston 11. The main case 10 has a lower end to which a lower cover 10b is attached. The lower cover 10b is formed with a lower end opening 10B for allowing vertical movement of the lancet B. The main case 10 defines a case chamber 10c which communicates, through the lower end opening 10B of the lower cover 10b, with the internal space of the cap 18 attached to the lower end of the lower cover 10b.

The piston 11 has an upper end 11a projecting from the head cover 10a through the upper end opening 10A. The piston 11 has a bottom portion 11b inserted in the case chamber 10c. In operation, the upper end 11a of the piston 11 is depressed by the user's finger or thumb for example. The bottom portion 11b of the piston 11 has an outer diameter which coincides with the inner diameter of the case chamber 10c. The bottom portion 11b of the piston 11 is formed, at the outer circumferential surface thereof, with an O-ring 11d which closely contacts the inner wall of the case chamber 10c for airtight sealing. With this arrangement, the piston 11 is airtightly movable up and down in the case chamber 10c.

The first plunger rod 12 is integral with the piston 11 and projects downward from the bottom portion 11b of the piston 11. The first plunger rod 12 is formed, at a longitudinally intermediate position thereof, with an engagement portion 12a which is tapered to provide a radially extending flat bottom surface. The first plunger rod 12 has a lower end integrally formed with a spring holder 12b. The spring holder 12b comprises a generally hollow cylinder for holding the spring 14 therein.

The first spring 13 has an upper end 13a fixed to the main case 10 and a lower end 13b fixed to the piston 11. As the piston 11 moves downward, the first spring 13 works to pull back the piston 11 upward by its elastic restoring force. Specifically, when the first spring 13, which is normally held in a state shown in FIG. 2, is tensioned, it elastically pulls back the piston 11 upwardly.

The second spring 14 has an upper end fixed to the spring holder 12b and a lower end fixed to the upper end of the second plunger rod 15. The second spring 14 works to elastically push back the first and the second plunger rods 12, 15 upward and downward, respectively. Specifically, when the second spring 14 is compressed from its normal state shown in FIG. 2 by the first and the second plunger rods 12, 15, it works to elastically push back these rods.

The second plunger rod 15 is connected, via the second spring 14, to a lower portion of the first plunger rod 12. The second plunger rod 15 is formed, at a longitudinally intermediate position thereof, with an engagement portion 15a which is tapered to provide a radially extending flat upper surface.

The lancet B is mounted to and held by the lancet mount 16. The lancet mount 16 is held by a third spring 17 in facing relationship to the lower end 15b of the second plunger rod 15 with a predetermined spacing therefrom. The lancet mount 16 is movable up and down in accordance with the elastic deformation of the third spring 17. It is to be noted that the lancet B is removable from the lancet mount 16 with the pointed tip B1 oriented downward.

The third spring 17 has an upper end 17a fixed to the lancet mount 16 and a lower end 17b fixed to the inner side of the lower cover 10b. When the lancet mount 16 is moved downward, the third spring 17 works to elastically force the lancet mount 16 upward for recovery to its normal position. Specifically, when the third spring 17 is compressed from its normal state shown in FIG. 2, it elastically pushes back the lancet mount 16 upward.

The cap 18 may be entirely formed of a transparent plastic material for example. The cap 18 is formed, at the end thereof, with an opening 18b. The cap 18 is fitted outwardly to the lower cover 10b of the main case 10. The cap 18 has an accommodation space 18a for accommodating the pointed tip B1 of the lancet B projecting through the lower opening 10B of the under cover 10. In sampling blood, the end of the cap 18 is pressed against the skin of the user to close the opening 18b.

The cap 18 is provided with an O-ring 18c for providing airtightness of the accommodation space 18a. Therefore, by closing the opening 18b with the skin, air is trapped in the accommodation space 18a through the case chamber 10c. The cap 18 is fitted over the lower cover 10b via threads (not shown) formed at the inner circumferential surface of the cap 18. The distance H from the opening 18b to the pointed tip B1 of the lancet B can be adjusted by varying the extent of screwing the cap 18.

The first latch mechanism 20 includes a first engagement member 21 having a stopper 21a corresponding to the engagement portion 12a of the first plunger rod 12, and a latch spring 22 for biasing the stopper 21a radially toward the first plunger rod 12. The first engagement member 21 is held as pressed against the outer circumferential surface of the first plunger rod 12. The latch spring 22 is provided at a predetermined position on the inner circumferential surface of the main case 10.

The second latch mechanism 26 includes a second engagement member 27 having a stopper 27a corresponding to the engagement portion 15a of the second plunger rod 15, and a latch spring 28 for biasing the stopper 27a radially toward the second plunger rod 15. The second engagement member 27 is held as pressed against the outer circumferential surface of the second plunger rod 15. The latch spring 28 is provided at a predetermined position on the inner circumferential surface of the main case 10.

The release mechanism 30 releases the first and the second plunger rods 12, 15 from the state restricted by the first and the second latch mechanisms 20, 26, respectively. The release mechanism 30 includes a release button 31 engaging the first and the second engagement members 21, 27 at positions opposite to the latch springs 22, 28, respectively, for simultaneously biasing these radially outward, a support member 32 for supporting the release button 31 within the case chamber 10c, and a shield member 33 interposed for keeping the airtightness between the release button 31 and the case chamber 10c. The release button 31 includes a push portion 31a projecting from a predetermined portion of the side surface of the main case 10. The shield member 33 comprises a film formed of a rubber for example.

The vacuum relief mechanism 40 serves to release the vacuum condition in the case chamber 10c after pushing the release button 31. As shown in FIG. 3, the vacuum relief mechanism 40 comprises a vacuum relief button 41 having a push portion 41a projecting through a port 10d provided at the side surface of the main case 10, a vacuum relief spring 42 for elastically biasing a flange portion 41b of the vacuum relief button 41 in facing relationship to the port 10d, and a nut 43 for holding the vacuum relief spring 42 within the case chamber 10c.

Next, the use and operation of the body fluid sampler A will be described with reference to FIGS. 2 and 4–8.

Figure 2:
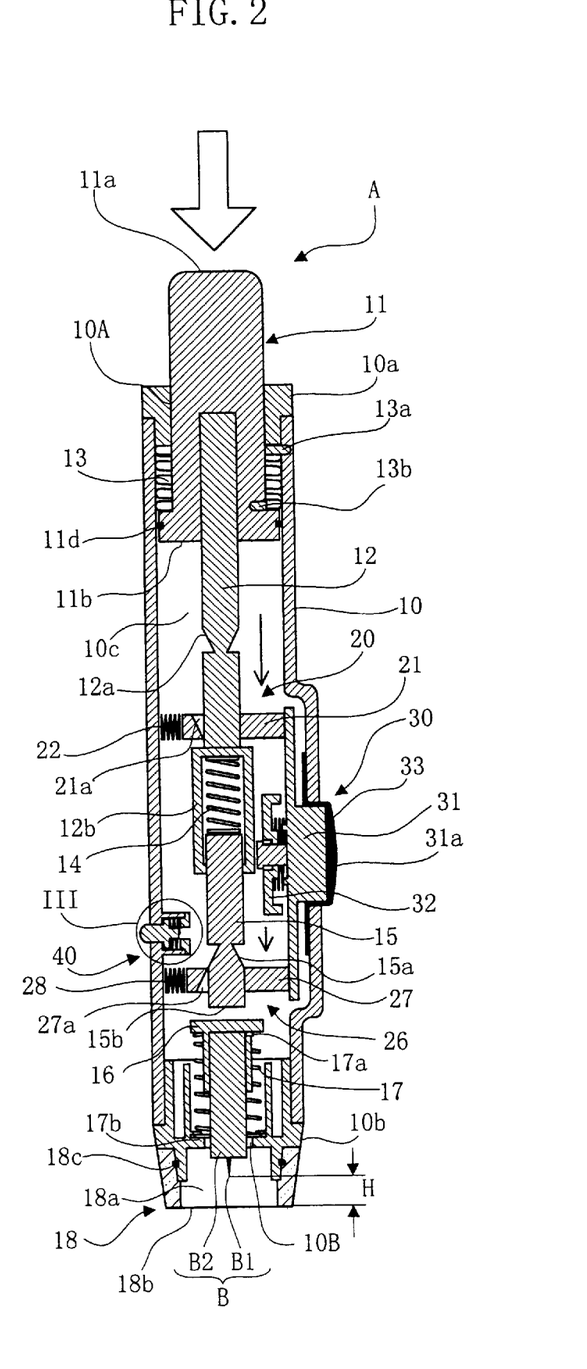
FIG. 2 is a sectional view taken on lines II—II of FIG. 1.
Figure 3:
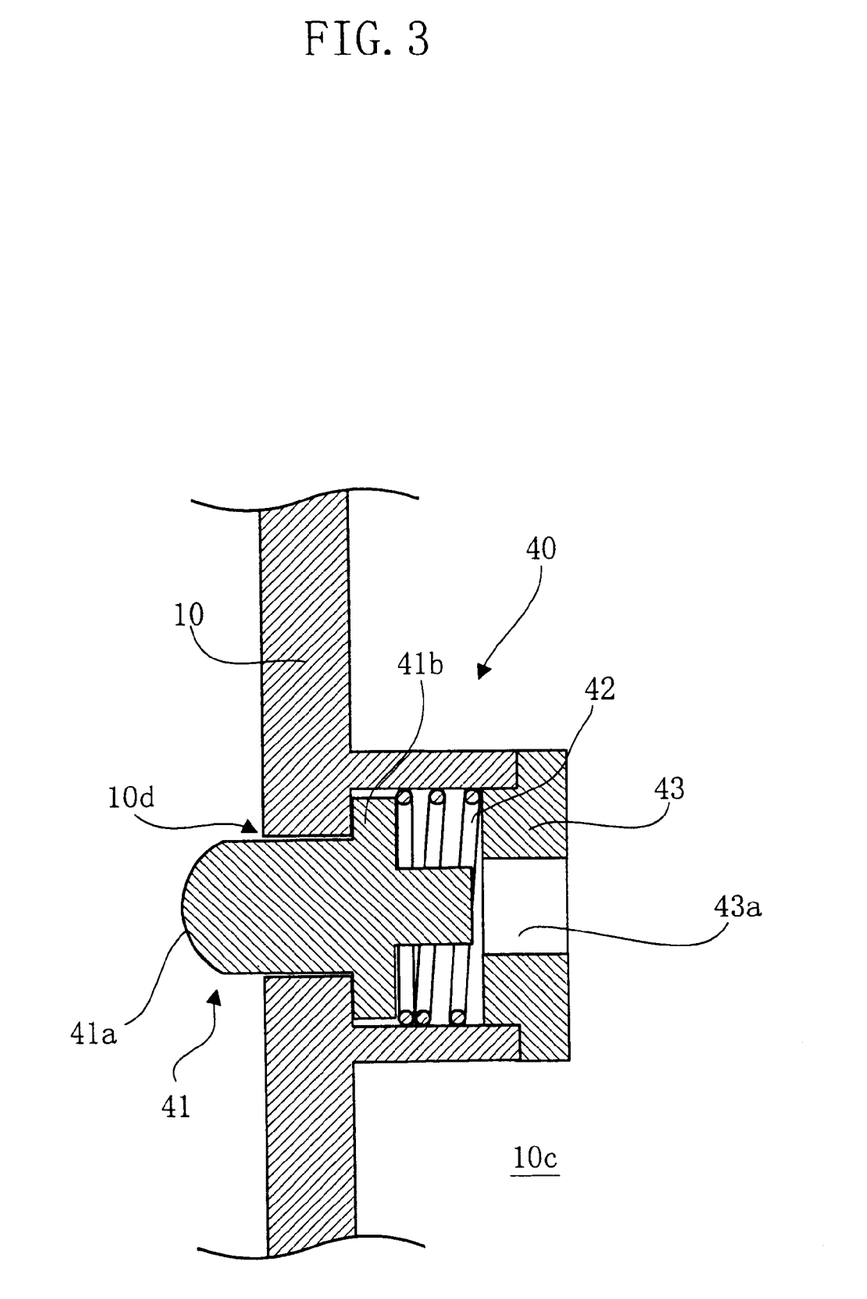
FIG. 3 is an enlarged sectional view showing a portion III of FIG. 2.

In the state shown in FIG. 2 (initial state), the stopper 21a, 27a of the first and the second engagement members 21, 27, are pressed against the first and the second plunger rods 12, 15, respectively, by the elastic biasing force of the relevant latch springs 22, 28.

In this state, the user performs a first operation. Specifically, the user pushes the upper end 11a of the piston 11 with the thumb for example to push down the piston 11. At this time, the user need not bring the opening 18b of the cap 18 into pressing contact with the skin. As a result, the piston 11 together with the first plunger rod 12 moves downward against the elastic restoring force of the first spring 13. Further, the second spring 14 and the second plunger rod 15 move downward accompanying the first plunger rod 12. In this case, the volume in the case chamber 10c gradually decreases as the bottom portion 11b of the piston 11 moves downward.

Figure 4:
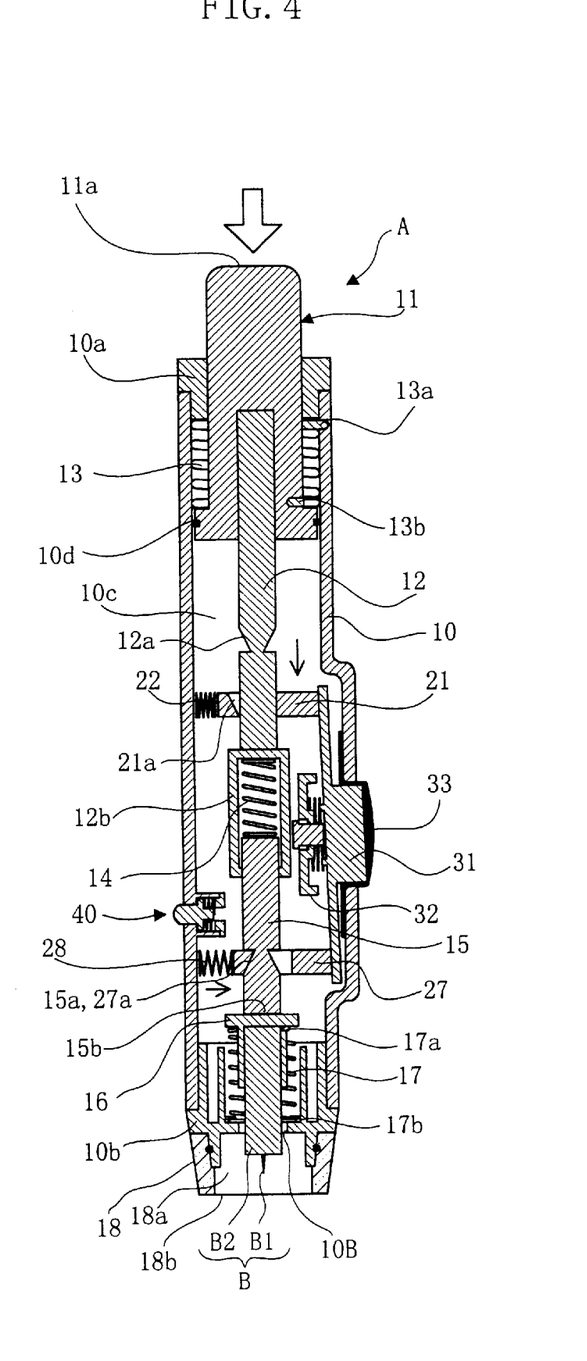
FIG. 4 is a sectional view showing the first operation of the body fluid sampler.

As shown in FIG. 4, when the piston 11 is progressively moved downward, the engagement portion 15a of the second plunger rod 15 comes into engagement with the stopper 27a of the second engagement member 27, making a click to be heard by the user. In this state, the second plunger rod 15 is unable to further move downward. At this time, the lower end 15b of the second plunger rod 15 is held in contact with the lancet mount 16 or held as slightly spaced therefrom.

Figure 5:
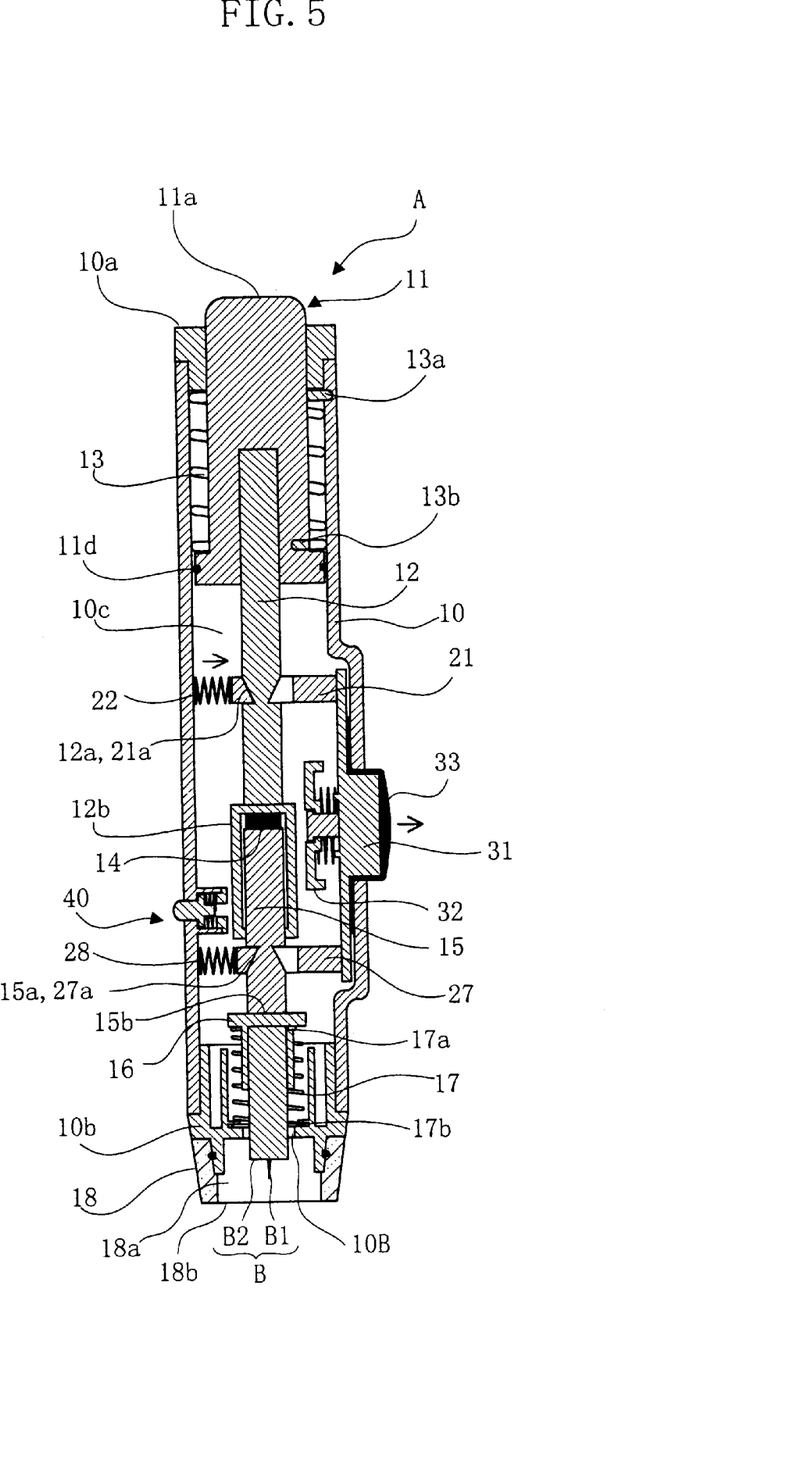
FIG. 5 is a sectional view showing the first operation of the body fluid sampler.

As shown in FIG. 5, when the piston 11 is further depressed, the engagement portion 12a of the first plunger rod 12 comes into engagement with the stopper 21a of the first engagement member 21, making a click to be heard by the user. In this state, the first plunger rod 12 is unable to further move upward. At this time, the second spring 14 is compressed between the first plunger rod 12 and the second plunger rod 15, thereby storing a sufficient elastic restoring force.

In this way, when the piston 11 is pushed downward, the engagement portion 15a of the second plunger rod 15 first engages the stopper 27a, and the engagement portion 12a of the first plunger rod 12 then engages the stopper 21a. For realizing such stepwise engaging movement, in the initial state of the plunger rods 12, 15, the distance between the vertically spaced two engagement portions 12a, 15a is set larger than the distance between the stoppers 21a and 27a of the first and the second engagement members 21, 27.

A preliminary operation before launching the lancet B is completed in the above-described manner. In this state, since the engagement portions 12a, 15a of the first and the second plunger rods 12, 15 are held in engagement with the stoppers 21a, 27a, respectively, the release button 31 slightly projects outward. The first spring 13 is tensioned approximately to its maximum length, and the volume in the case chamber 10c is kept minimum because the bottom portion 11b of the piston 11 has moved to the lowest limit position.

Figure 6:
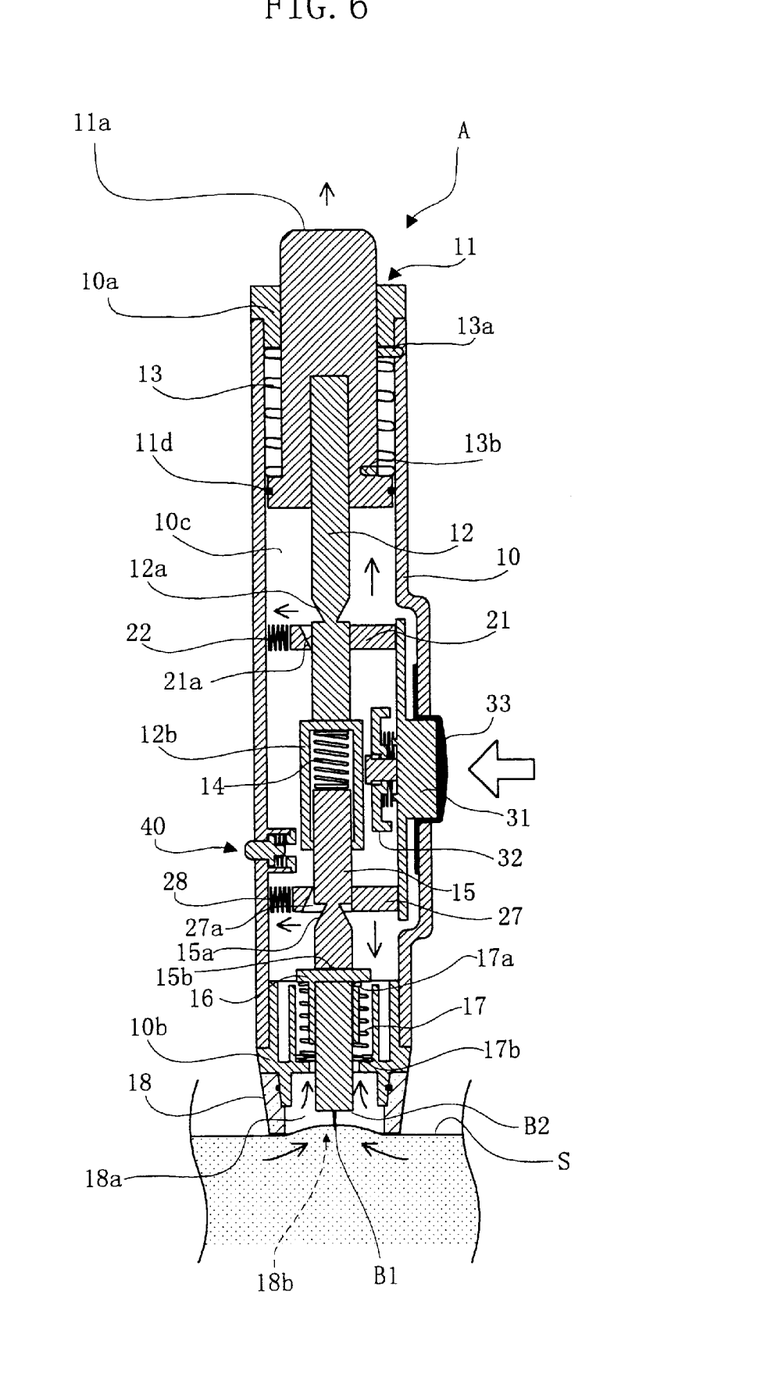
FIG. 6 is a sectional view showing the second operation of the body fluid sampler.

Subsequently, as shown in FIG. 6, the body fluid sampler A is pressed against the skin S to close the opening 18b of the cap 18 with the skin. Then, as a second operation, the release button 31 is pushed by the user radially of the main case 10. FIG. 6 illustrates the state immediately after the release button 31 is pushed.

As a result, the first and the second plunger rods 12, 15 which have been restricted by the first and the second engagement members 21, 27 are simultaneously released from the respective stoppers 21a, 27a. The first and the second plunger rods 12, 15 quickly move upward and downward, respectively, in a mutually repelling manner due to the elastic restoring force of the second spring 14. Thus, the second plunger rod 15 strongly hits or pushes the lancet mount 16 downward. Therefore, the pointed tip B1 of the lancet B integrally provided on the lancet mount 16 moves toward the opening 18b to instantaneously stab the skin S. Then, the pointed tip B1 of the lancet B is removed from the skin S due to the elastic restoring force of the third spring 17.

On the other hand, the first plunger rod 12 is pulled back and held at a position close to the initial position together with the piston 11 pulled back upward due to the elastic restoring force of the first spring 13. At this time, the opening 18b of the cap 18 of the case chamber 10c is closed with the skin S. Therefore, as the piston 11 moves upward, the volume of the case chamber 10c gradually increases.

The pressure in the case chamber 10c is reduced to a subatmospheric pressure so that the pressure in the accommodation space 18a of the cap 18, which communicates with the case chamber 10c, is also reduced. Since the shield member 33 is provided at the clearance between the release button 31 and the case chamber 10c, the case chamber 10c is prevented from air leakage relative to the outside. Therefore, the skin S closing the opening 18b of the cap 18 bulges due to the suction of the vacuum. As a result, bleeding is accelerated from the portion stabbed by the pointed tip B1 of the lancet B. The bleeding state can be observed by the user through the transparent cap 18.

Figure 7:
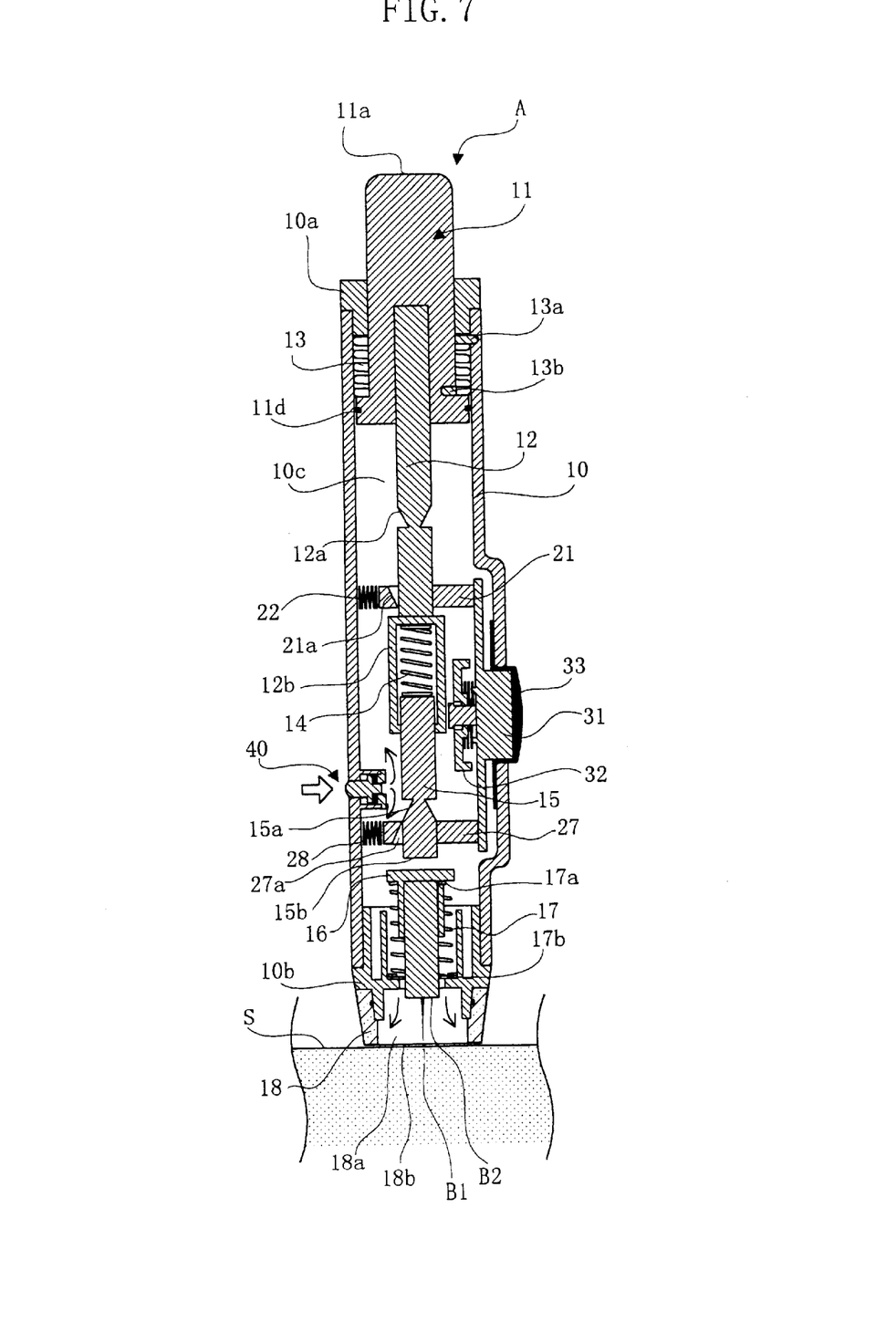
FIG. 7 is a sectional view showing the third operation of the body fluid sampler.
Figure 8:
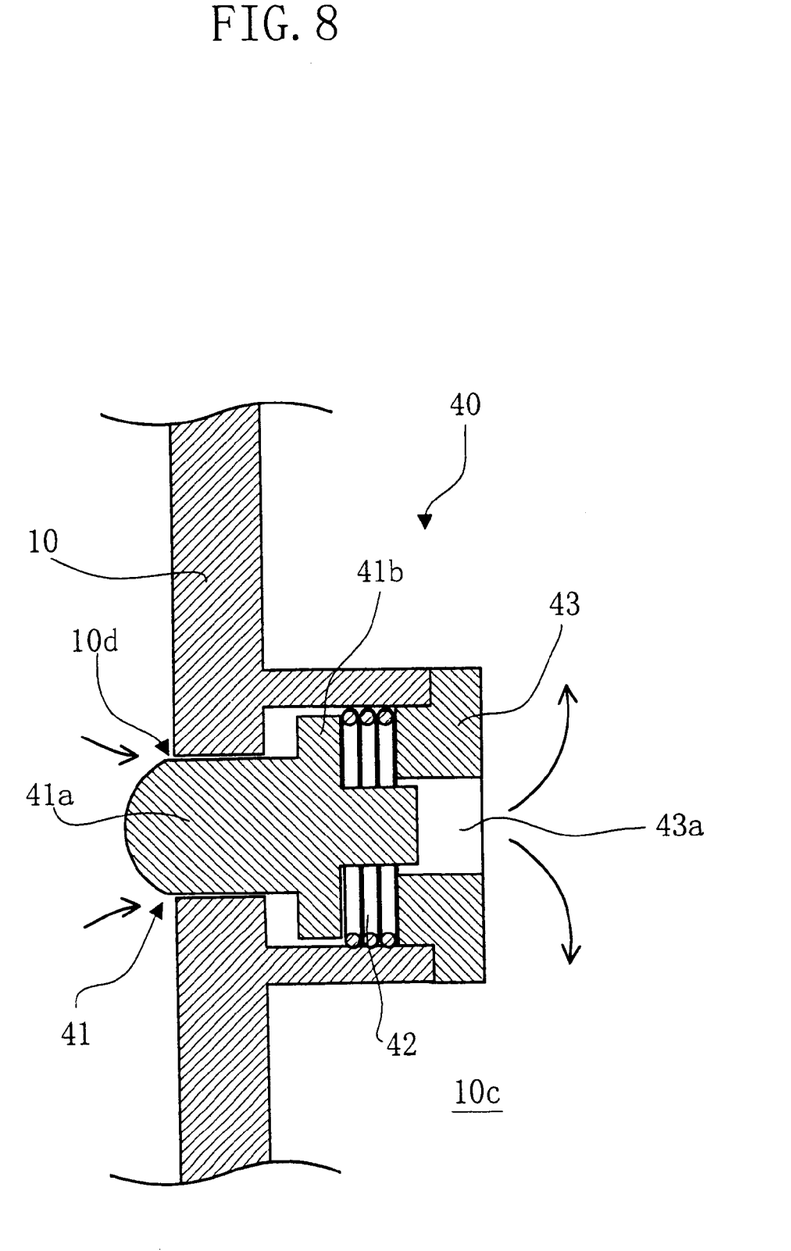
FIG. 8 is an enlarged sectional view of the principal portion shown in FIG. 7.

Next, as a third operation, the vacuum relief button 41 of the vacuum relief mechanism 40 is pushed by the user, as shown in FIGS. 7 and 8. As a result, air is introduced from the outside through the port 10d formed in the main case 10 and a hole 43a of the nut 43 into the case chamber 10c. Thus, the pressure in the case chamber 10c returns to the initial atmospheric pressure. Similarly, the pressure in the accommodation space 18a communicating with the case chamber 10c returns to the atmospheric pressure. Therefore, the skin S closing the opening 18b of the cap 18 is relieved from the vacuum sucked state. Therefore, the opening 18b of the cap 18 can be easily removed from the skin S.

In this way, according to the body fluid sampler A, the preparation for launching the lancet B can be completed by one-push operation. Further, the subsequent launching of the lancet B can be completed just by once pushing the release button 31. The first operation of pushing down the piston 11 can be performed under the atmospheric pressure. Therefore, the user needs only to push down the piston 11 by a predetermined stroke without using a strong force. Thus, the user can operate the apparatus easily without anxiety.

The vacuum state of the case chamber 10c is relieved by pushing the vacuum relief button 41. The vacuum relief button 41 is provided separately from the release button 31 for launching the lancet B, which decreases the possibility of erroneously launching the lancet B. Therefore, the user can handle the apparatus safely.

It is to be noted that the present invention is not limited to the above-described embodiment. For example, although coiled springs are utilized for launching the lancet B and for reducing the pressure in the case chamber 10c, any other elastic members may be used if only they can be elastically compressed and restored sufficiently.

Moreover, although the body fluid sampler A is preferably used for self-sampling blood, the apparatus may be used for sampling body fluid other than blood, which can be sampled through the skin.

What is claimed is:

1. A body fluid sampler comprising:
   a cylindrical main case having a first end provided with a first opening and a second end provided with a second opening;
   a piston inserted in the main case to project from the first opening for movement within the main case airtightly with respect to an inner wall of the main case;
   a first plunger rod extending integrally from the piston toward said second end;
   a first elastic member for elastically urging the piston toward said first end;

a second plunger rod extending from the first plunger rod toward said second end for movement within the main case with a compressible second elastic member interposed between the first plunger rod and the second plunger rod;

a lancet mount associated with the second plunger rod adjacent to said second end for movement within the main case, the lancet mount being provided with a lancet oriented toward said second end;

a third elastic member for elastically urging the lancet mount toward said first end;

a latch mechanism which works, when the piston is pushed down for movement toward said second end together with the first plunger rod, for restricting movement of the second plunger rod toward said second end against a pushing force of the second elastic member and for restricting rebounding of the piston and first plunger rod which have been moved toward said second end while allowing the second elastic member to be compressed; and a release mechanism for releasing the first plunger rod and second plunger rod which have been latched by the latch mechanism.

2. The body fluid sampler according to claim 1, wherein the latch mechanism includes:

a first and a second engagement members each of which has a stopper for stopping a corresponding one of the first and the second plunger rods;

a latching elastic member for elastically biasing each of the engagement members toward the corresponding one of the first and the second plunger rods; and engagement portions respectively formed on the first and the second plunger rods, the engagement portions being spaced from each other by a distance which is larger than a distance between the stoppers when the plunger rods are held in an initial state;

the release mechanism including:

a release button for simultaneously releasing the stoppers from the corresponding engagement portions against an elastic biasing force of the latching elastic member.

3. The body fluid sampler according to claim 2, wherein the release button is provided with a push portion projecting from a predetermined portion of a side surface of the main case while keeping airtightness relative to the main case.

4. The body fluid sampler according to claim 1, wherein the main case is provided with a vacuum relief mechanism for relieving a vacuum state within the main case generated by pulling back the piston toward said first end.

5. The body fluid sampler according to claim 4, wherein the vacuum relief mechanism is provided with a vacuum relief button partially projecting from a predetermined portion of a side surface of the main case, the vacuum relief button being elastically urged in the projecting direction while keeping airtightness of the main case, the vacuum relief button being pushed against the elastic urging force for allowing air passage between inside and outside of the main case.

6. The body fluid sampler according to claim 1, wherein the piston has an outer circumferential wall provided with an O-ring for closely contacting the inner wall of the main case.

* * * * *